US008060214B2

(12) United States Patent  (10) Patent No.: US 8,060,214 B2
Larson et al.  (45) Date of Patent: Nov. 15, 2011

(54) IMPLANTABLE MEDICAL DEVICE WITH INDUCTIVE COIL CONFIGURABLE FOR MECHANICAL FIXATION

(75) Inventors: Dennis E. Larson, White Bear, MN (US); Cheng Zhang, Vadnais Heights, MN (US); Keith R. Maile, New Brighton, MN (US); Abhi V. Chavan, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 939 days.

(21) Appl. No.: 11/326,802

(22) Filed: Jan. 5, 2006

(65) Prior Publication Data
US 2007/0156205 A1  Jul. 5, 2007

(51) Int. Cl.
*A61N 1/00* (2006.01)
*A61N 1/08* (2006.01)
(52) U.S. Cl. ............... 607/61; 607/16; 607/60
(58) Field of Classification Search ......... 600/109, 600/160, 300, 345, 385, 476; 607/17, 29–36, 607/3, 9, 60–66, 16; 128/903; 348/45, 76–77
See application file for complete search history.

(56) References Cited

U.S. PATENT DOCUMENTS

| 3,874,388 A | 4/1975 | King et al. |
| 4,391,124 A | 7/1983 | Drost et al. |
| 4,407,296 A | 10/1983 | Anderson |
| 4,485,813 A | 12/1984 | Anderson et al. |
| 4,492,107 A | 1/1985 | Sandhu |
| 4,672,976 A | 6/1987 | Kroll |
| 4,836,204 A | 6/1989 | Landymore et al. |
| 4,846,191 A | 7/1989 | Brockway et al. |
| 4,900,303 A | 2/1990 | Lemelson |
| 4,917,089 A | 4/1990 | Sideris |
| 4,966,148 A | 10/1990 | Millar |
| 5,040,538 A | 8/1991 | Mortazavi |
| 5,218,965 A | 6/1993 | Ring |

(Continued)

FOREIGN PATENT DOCUMENTS
EP  0897690  2/1999
(Continued)

OTHER PUBLICATIONS

International Search Report and Written Opinion of International Application No. PCT/US2007/060041, filed Jan. 3, 2007, both dated Jul. 13, 2007.

(Continued)

*Primary Examiner* — Unsu Jung
*Assistant Examiner* — Lawrence Laryea
(74) *Attorney, Agent, or Firm* — Faegre & Benson LLP

(57) ABSTRACT

An embodiment of a system for gathering physiologic data related to a human body includes a sensor device implanted in the human body, an inductive coil communicably coupled to the implanted sensor device; and a manager device in communication with the implanted sensor device via the inductive coil. The coil may be wrapped around the sensor device or attached to the sensor device fixation. An embodiment of a method for gathering physiologic data related to a physiologic parameter in a human body includes communicably coupling an inductive coil to communication circuitry of an implantable medical device (IMD), deploying the inductive coil and the IMD into a vessel of the human body, and inducing current in the inductive coil via the communication circuitry, the current representative of data associated with the IMD.

22 Claims, 7 Drawing Sheets

U.S. PATENT DOCUMENTS

| | | | |
|---|---|---|---|
| 5,284,138 A | 2/1994 | Kujawski | |
| 5,303,207 A | 4/1994 | Brady et al. | |
| 5,334,217 A | 8/1994 | Das | |
| 5,411,551 A | 5/1995 | Winston et al. | |
| 5,415,630 A | 5/1995 | Gory et al. | |
| 5,451,235 A | 9/1995 | Lock et al. | |
| 5,604,531 A * | 2/1997 | Iddan et al. | 348/76 |
| 5,634,936 A | 6/1997 | Linden et al. | |
| 5,656,036 A | 8/1997 | Palmaz | |
| 5,662,711 A | 9/1997 | Douglas | |
| 5,704,352 A | 1/1998 | Tremblay et al. | |
| 5,725,552 A | 3/1998 | Kotula et al. | |
| 5,733,313 A * | 3/1998 | Barreras et al. | 607/33 |
| 5,772,669 A | 6/1998 | Vrba | |
| 5,775,331 A | 7/1998 | Raymond et al. | |
| 5,824,053 A | 10/1998 | Khosravi et al. | |
| 5,833,603 A | 11/1998 | Kovacs et al. | |
| 5,855,563 A | 1/1999 | Kaplan et al. | |
| 5,860,923 A | 1/1999 | Lenker et al. | |
| 5,891,154 A | 4/1999 | Loeffler | |
| 5,967,980 A | 10/1999 | Ferre et al. | |
| 5,967,986 A | 10/1999 | Cimochowski et al. | |
| 5,967,989 A | 10/1999 | Cimochowski et al. | |
| 6,002,969 A | 12/1999 | Machek et al. | |
| 6,015,386 A | 1/2000 | Kensey et al. | |
| 6,015,387 A | 1/2000 | Schwartz et al. | |
| 6,030,413 A | 2/2000 | Lazarus | |
| 6,033,366 A | 3/2000 | Brockway et al. | |
| 6,053,873 A | 4/2000 | Govari et al. | |
| 6,076,016 A | 6/2000 | Feierbach | |
| 6,097,984 A | 8/2000 | Douglas | |
| 6,106,464 A | 8/2000 | Bass et al. | |
| 6,140,740 A | 10/2000 | Porat et al. | |
| 6,159,156 A | 12/2000 | Van Bockel | |
| 6,161,029 A * | 12/2000 | Spreigl et al. | 600/381 |
| 6,179,858 B1 | 1/2001 | Squire et al. | |
| 6,193,745 B1 | 2/2001 | Fogarty et al. | |
| 6,214,025 B1 | 4/2001 | Thistle et al. | |
| 6,231,516 B1 * | 5/2001 | Keilman et al. | 600/485 |
| 6,236,889 B1 | 5/2001 | Soykan et al. | |
| 6,239,724 B1 | 5/2001 | Doron et al. | |
| 6,240,312 B1 * | 5/2001 | Alfano et al. | 600/476 |
| 6,246,898 B1 | 6/2001 | Vesely et al. | |
| 6,277,078 B1 | 8/2001 | Porat et al. | |
| 6,278,790 B1 | 8/2001 | Davis et al. | |
| 6,309,350 B1 | 10/2001 | Van Tassel | |
| 6,328,699 B1 | 12/2001 | Eigler et al. | |
| 6,331,163 B1 | 12/2001 | Kaplan | |
| 6,379,308 B1 | 4/2002 | Brockway et al. | |
| 6,409,674 B1 | 6/2002 | Brockway et al. | |
| 6,416,474 B1 | 7/2002 | Penner et al. | |
| 6,432,050 B1 | 8/2002 | Porat et al. | |
| 6,442,413 B1 | 8/2002 | Silver | |
| 6,447,522 B2 | 9/2002 | Gambale et al. | |
| 6,475,170 B1 | 11/2002 | Doran et al. | |
| 6,486,588 B2 | 11/2002 | Doron et al. | |
| 6,527,780 B1 | 3/2003 | Wallace et al. | |
| 6,543,272 B1 | 4/2003 | Vitek | |
| 6,585,763 B1 | 7/2003 | Keilman et al. | |
| 6,592,553 B2 | 7/2003 | Zhang et al. | |
| 6,628,989 B1 | 9/2003 | Penner et al. | |
| 6,660,021 B1 | 12/2003 | Palmer et al. | |
| 6,685,638 B1 | 2/2004 | Taylor et al. | |
| 6,699,186 B1 | 3/2004 | Wolinsky et al. | |
| 6,702,847 B2 | 3/2004 | DiCarlo | |
| 6,730,108 B2 | 5/2004 | Van Tassel et al. | |
| 6,743,173 B2 | 6/2004 | Penner et al. | |
| 6,746,404 B2 | 6/2004 | Schwartz | |
| 6,747,916 B1 | 6/2004 | Fluery et al. | |
| 6,755,855 B2 | 6/2004 | Yurek et al. | |
| 6,764,446 B2 | 7/2004 | Wolinsky et al. | |
| 6,783,499 B2 | 8/2004 | Schwartz | |
| 6,800,060 B2 * | 10/2004 | Marshall | 600/309 |
| 6,840,956 B1 | 1/2005 | Wolinsky et al. | |
| 6,855,115 B2 | 2/2005 | Fonseca et al. | |
| 6,868,288 B2 | 3/2005 | Thompson | |
| 6,890,303 B2 | 5/2005 | Fitz | |
| 6,899,729 B1 | 5/2005 | Cox | |
| 6,920,347 B2 | 7/2005 | Simon et al. | |
| 6,926,670 B2 | 8/2005 | Rich | |
| 6,934,573 B1 * | 8/2005 | Glukhovsky et al. | 600/407 |
| 6,950,690 B1 * | 9/2005 | Meron et al. | 600/424 |
| 6,958,034 B2 * | 10/2005 | Iddan | 600/114 |
| 6,970,742 B2 | 11/2005 | Mann et al. | |
| 6,972,017 B2 | 12/2005 | Smith et al. | |
| 6,984,205 B2 * | 1/2006 | Gazdzinski | 600/160 |
| 7,001,329 B2 * | 2/2006 | Kobayashi et al. | 600/114 |
| 7,006,858 B2 | 2/2006 | Silver et al. | |
| 7,009,634 B2 * | 3/2006 | Iddan et al. | 348/76 |
| 7,011,671 B2 | 3/2006 | Welch | |
| 7,024,248 B2 | 4/2006 | Penner et al. | |
| 7,035,684 B2 | 4/2006 | Lee | |
| 7,039,453 B2 * | 5/2006 | Mullick et al. | 600/476 |
| 7,060,038 B2 | 6/2006 | Letort et al. | |
| 7,064,472 B2 | 6/2006 | Peline et al. | |
| 7,083,822 B2 | 8/2006 | Brightbill | |
| 7,116,352 B2 * | 10/2006 | Yaron | 348/45 |
| 7,118,529 B2 * | 10/2006 | Glukhovsky et al. | 600/160 |
| 7,118,531 B2 | 10/2006 | Krill | |
| 7,131,986 B2 | 11/2006 | Sirhan et al. | |
| 7,160,258 B2 * | 1/2007 | Imran et al. | 600/593 |
| 7,181,261 B2 | 2/2007 | Silver et al. | |
| 7,198,603 B2 | 4/2007 | Penner et al. | |
| 7,211,045 B2 | 5/2007 | Dala-Krishna et al. | |
| 7,273,457 B2 * | 9/2007 | Penner | 600/561 |
| 7,283,874 B2 | 10/2007 | Penner | |
| 7,308,319 B2 | 12/2007 | Lovett et al. | |
| 7,338,512 B2 | 3/2008 | McGuckin, Jr. et al. | |
| 7,347,868 B2 | 3/2008 | Burnett et al. | |
| 7,452,334 B2 | 11/2008 | Gianchandani et al. | |
| 7,477,946 B2 | 1/2009 | Tockman et al. | |
| 7,780,694 B2 | 8/2010 | Palmer et al. | |
| 7,850,708 B2 | 12/2010 | Pal | |
| 2002/0026228 A1 * | 2/2002 | Schauerte | 607/122 |
| 2002/0072656 A1 * | 6/2002 | Vantassel et al. | 600/300 |
| 2002/0103417 A1 * | 8/2002 | Gazdzinski | 600/109 |
| 2002/0123672 A1 | 9/2002 | Christophersom et al. | |
| 2002/0128546 A1 * | 9/2002 | Silver | 600/365 |
| 2002/0165601 A1 | 11/2002 | Clerc | |
| 2002/0173718 A1 * | 11/2002 | Frisch et al. | 600/424 |
| 2002/0183628 A1 | 12/2002 | Reich et al. | |
| 2002/0188207 A1 | 12/2002 | Richter | |
| 2003/0114897 A1 | 6/2003 | Von Arx et al. | |
| 2003/0139796 A1 | 7/2003 | Sequin et al. | |
| 2003/0163187 A1 * | 8/2003 | Weber | 623/1.2 |
| 2003/0200031 A1 | 10/2003 | de Kok | |
| 2003/0204223 A1 * | 10/2003 | Leinders et al. | 607/48 |
| 2004/0006377 A1 | 1/2004 | Behm | |
| 2004/0059392 A1 * | 3/2004 | Parramon et al. | 607/36 |
| 2004/0116981 A1 | 6/2004 | Mazar | |
| 2004/0116992 A1 | 6/2004 | Wardle et al. | |
| 2004/0147969 A1 * | 7/2004 | Mann et al. | 607/17 |
| 2004/0176672 A1 | 9/2004 | Silver et al. | |
| 2004/0204744 A1 | 10/2004 | Penner et al. | |
| 2004/0215228 A1 | 10/2004 | Simpson et al. | |
| 2005/0080472 A1 | 4/2005 | Atkinson et al. | |
| 2005/0115561 A1 | 6/2005 | Stahmann et al. | |
| 2005/0124875 A1 * | 6/2005 | Kawano et al. | 600/407 |
| 2005/0136385 A1 | 6/2005 | Mann et al. | |
| 2005/0149108 A1 | 7/2005 | Cox | |
| 2005/0149128 A1 | 7/2005 | Heil, Jr. et al. | |
| 2005/0149155 A1 | 7/2005 | Scheiner et al. | |
| 2005/0149156 A1 | 7/2005 | Libbus et al. | |
| 2005/0154321 A1 | 7/2005 | Wolinsky et al. | |
| 2005/0165456 A1 | 7/2005 | Mann et al. | |
| 2005/0209678 A1 | 9/2005 | Henkes et al. | |
| 2005/0245840 A1 | 11/2005 | Christopherson et al. | |
| 2006/0009818 A1 | 1/2006 | Von Arx et al. | |
| 2006/0047205 A1 | 3/2006 | Ludomirsky et al. | |
| 2006/0064133 A1 | 3/2006 | Von Arx et al. | |
| 2006/0064134 A1 | 3/2006 | Mazar et al. | |
| 2006/0064142 A1 | 3/2006 | Chavan et al. | |
| 2006/0064143 A1 | 3/2006 | Von Arx et al. | |
| 2006/0079740 A1 | 4/2006 | Silver et al. | |
| 2006/0089627 A1 | 4/2006 | Burnett et al. | |
| 2006/0089694 A1 | 4/2006 | Zhang et al. | |
| 2006/0122522 A1 | 6/2006 | Chavan et al. | |

| | | | |
|---|---|---|---|
| 2006/0136004 A1 | 6/2006 | Cowan et al. | |
| 2006/0142819 A1 | 6/2006 | Penner et al. | |
| 2006/0149329 A1 | 7/2006 | Penner | |
| 2006/0149330 A1 | 7/2006 | Mann et al. | |
| 2006/0178586 A1 | 8/2006 | Dobak, III | |
| 2006/0206153 A1 | 9/2006 | Libbus et al. | |
| 2006/0241735 A1 | 10/2006 | Tockman et al. | |
| 2006/0259085 A1 | 11/2006 | Zhang et al. | |
| 2006/0287700 A1 | 12/2006 | White et al. | |
| 2006/0293741 A1 | 12/2006 | Johnson et al. | |
| 2007/0049833 A1* | 3/2007 | Tearney et al. | 600/476 |
| 2007/0129637 A1 | 6/2007 | Wolinsky et al. | |
| 2007/0150009 A1* | 6/2007 | Kveen et al. | 607/9 |
| 2007/0156126 A1 | 7/2007 | Flaherty | |
| 2007/0162090 A1 | 7/2007 | Penner | |
| 2007/0179583 A1 | 8/2007 | Goetzinger et al. | |
| 2007/0191904 A1 | 8/2007 | Libbus et al. | |
| 2007/0208390 A1 | 9/2007 | Von Arx et al. | |
| 2007/0250126 A1 | 10/2007 | Maile et al. | |
| 2007/0274565 A1 | 11/2007 | Penner | |
| 2008/0071178 A1 | 3/2008 | Greenland et al. | |
| 2008/0071248 A1 | 3/2008 | Delgado et al. | |
| 2008/0071339 A1 | 3/2008 | Stalker et al. | |
| 2008/0108904 A1 | 5/2008 | Heil | |
| 2008/0176271 A1 | 7/2008 | Silver et al. | |
| 2008/0275350 A1 | 11/2008 | Liao et al. | |
| 2008/0283066 A1 | 11/2008 | Delgado et al. | |
| 2009/0054793 A1 | 2/2009 | Nunez et al. | |
| 2009/0171274 A1 | 7/2009 | Harlev et al. | |
| 2009/0270742 A1 | 10/2009 | Wolinsky et al. | |
| 2010/0016840 A1 | 1/2010 | Stahmann et al. | |
| 2010/0210923 A1 | 8/2010 | Li et al. | |

FOREIGN PATENT DOCUMENTS

| | | |
|---|---|---|
| EP | 0928598 | 8/2000 |
| EP | 1068836 | 1/2001 |
| EP | 1488735 | 6/2007 |
| GB | 2333044 | 7/1999 |
| JP | H(11)-089942 | 4/1999 |
| JP | 2000-507142 | 6/2000 |
| WO | WO83/03348 | 10/1983 |
| WO | WO99/34731 | 7/1999 |
| WO | WO00/16686 | 3/2000 |
| WO | WO01/67989 | 9/2001 |
| WO | WO01/87137 | 11/2001 |
| WO | WO 2004/024034 | 3/2004 |
| WO | WO2005/067817 | 7/2005 |
| WO | WO2006/062725 | 6/2006 |
| WO | WO2007/057739 | 5/2007 |
| WO | 2008002654 | 1/2008 |
| WO | WO2008/034077 | 3/2008 |
| WO | WO2008/057720 | 5/2008 |
| WO | WO2008/060197 | 5/2008 |
| WO | 2009006610 | 1/2009 |

OTHER PUBLICATIONS

Holmes et al. "SirolimusEluting Stents vs. Vascular Brachytherapy for InStent Restenosis Within BareMetal Stents" JAMA 295 (11): 1264-1273 Mar. 15, 2006.

Lanning & Shandas, "Development and Validation of Implantable Sensors for Monitoring Function of Prosthetic Heart Valves: In Vitro Studies", Medical & Biological Engineering & Computing, Jul. 2003, vol. 41, issue 4, pp. 416-424.

Sheth et al. "Subacute Thrombosis and Vascular Injury Resulting From Slotted-Tube Nitinol and Stainless Steel Stents in a Rabbit Carotid Artery Model" Circulation 1996, 94: 1733-1740.

Stone et al. "Paclitaxel-Eluting Stents vs.Vascular Brachytherapy for In-Stent Restenosis Within Bare-Metal Stents" JAMA 295( 11): 1253-1263, Mar. 15, 2006.

Wenaweser et al. "Stent thrombosis following baremetal stent implantation: success of emergency percutaneous coronary intervention and predictors of adverse outcome" European Heart Journal 26: 1180-1187 2005.

Goodall, Eleanor V. et al., "Position-Seletive Activation of Peripheral Nerve Fibers with a Cuff Electrode", IEEE Transactions on Biomedical Engineering, IEEE Service Center, Piscataway, NJ, US, vol. 43, No. 8, Aug. 1, 1996.

International Search Report and Written Opinion issued in PCT/US2010/020756, mailed Sep. 27, 2010.

Invitation to Pay Fees and Partial Search Report issued in PCT/US2010/020756, mailed May 12, 2010.

* cited by examiner

IMPLANTABLE MEDICAL DEVICE WITH INDUCTIVE COIL CONFIGURABLE FOR MECHANICAL FIXATION

TECHNICAL FIELD

The present invention relates generally to an inductive coil configured for energy delivery and/or data communication to/from an implantable medical device. More specifically, the inductive coil may be configured for mechanically fixing the implantable medical device at a location in a human body.

BACKGROUND

Medical devices can be implanted in the bodies of patients for various purposes. Some medical devices detect physiologic events and may apply therapy in response to certain events of interest. For example, a cardiac pacemaker can detect a lull in the beating of the patient's heart and apply an electrical pulse to stimulate the heart into beating again. Implantable sensors are preferably small so that they can be maneuvered and deployed in areas of the human body that are difficult to access.

Implantable sensor devices typically include components that require power to operate. For example, the sensor may require some small amount of power to sense the physiologic parameter of interest (e.g., blood pressure). An implantable sensor device may also have the ability to transmit and receive data via communications circuitry that requires power. As such, implantable sensor devices typically include a battery.

Some implantable sensor devices are connected by wires to another device, such as pulse generator, which is also implanted in the body. The wires can be used for communication to and from the other device and/or for power delivery. These wires can add to the difficulty in maneuvering and deploying the implantable sensor in the body, particularly at locations that are not easily accessible.

SUMMARY

Embodiments described herein include systems, devices, and methods for delivering electric energy to and/or communicating with an implantable medical device via an inductive coil disposed around or near the implantable medical device (IMD). The IMD can communicate by generating an oscillating current in the inductive coil, thereby creating an electromagnetic field that can be sensed by another device. Another device can communicate with the IMD by generating an oscillating electromagnetic field that induces electromotive force (EMF) in the coil when the electromagnetic field crosses the inductive coil. In addition, when the inductive coil is disposed around the IMD, the coil can anchor the IMD at a location in a bodily vessel by expanding against walls of the bodily vessel.

An embodiment of a system for anchoring an implantable medical device (IMD) at a location within a vessel of a human body includes an inductive coil having a first electrode coupled to a high voltage node in the implantable medical device, and a second electrode connected to a low voltage node in the IMD, wherein an electromagnetic field induced near the inductive coil generates EMF in the inductive coil, and wherein the inductive coil expands against opposing walls of the vessel to frictionally anchor the IMD at the location.

An embodiment of a system for gathering physiologic data related to a human body includes a sensor device implanted in the human body, an inductive coil communicably coupled to the implanted sensor device, and a manager device in communication with the implanted sensor device via the inductive coil.

An embodiment of a method for gathering physiologic data related to a physiologic parameter in a human body includes communicably coupling an inductive coil to communication circuitry of an implantable medical device (IMD), deploying the inductive coil and the IMD into a vessel of the human body, and inducing oscillating current in the inductive coil via the communication circuitry, the oscillating current generating an electromagnetic field comprising a signal representative of data associated with the IMD.

An embodiment of a system for implanting a sensor device in a human body includes a sensor device having a casing that houses a communication module, a battery recharge module, a sensor operable to sense a physiologic parameter, and a rechargeable battery. The system further includes means for anchoring the sensor device at a location in the human body, wherein the means for anchoring provides at least one of communication and energy delivery to the sensor device.

An embodiment of an exemplary system includes a sensor device implanted in the human body, an inductive coil communicably coupled to the implanted sensor device, and a manager device in communication with the implanted sensor device via the inductive coil. The manager device can include or be housed in a pulse generator implanted in the human body. The manager device may be a nontherapeutic device implanted in the human body. The manager device may be operable to command the implanted sensor device to transmit physiologic data via the inductive coil. The implanted sensor device may further include a rechargeable battery coupled to the inductive coil.

In embodiments of some systems, an implanted sensor device includes a communication module coupled to an inductive coil. The communication module may be operable to receive a command from a manager device via the inductive coil. The communication module may be further operable to transmit data in response to receiving the command. The implanted sensor device can further include a sensor device controller that can detect recharging of the battery and deactivate at least a portion of the communication module in response to detecting recharging of the battery. A battery recharge controller can be included to detect a recharge signal from the inductive coil and use the signal to recharge the battery.

In some embodiments, electrodes of an inductive coil are disposed through insulative feedthroughs positioned in a wall of an IMD. The feedthrough may be composed of a biocompatible insulator. For example, the feedthroughs may be composed of a material selected from a group consisting of thermoplastic polyurethane, and alumina.

In yet another embodiment, an inductive coil may comprise an attachment to an implanted sensor device. In some embodiments of the system the inductive coil forms a stent-like structure coiled around an implanted sensor device. The inductive coil can be an attachment to the fixation. The stent-like structure can expand against walls of a vessel in the human body to provide fixation within the vessel.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the scope of the present invention. Accordingly, the drawings and detailed description are to be regarded as illustrative in nature and not restrictive.

Figure 1:
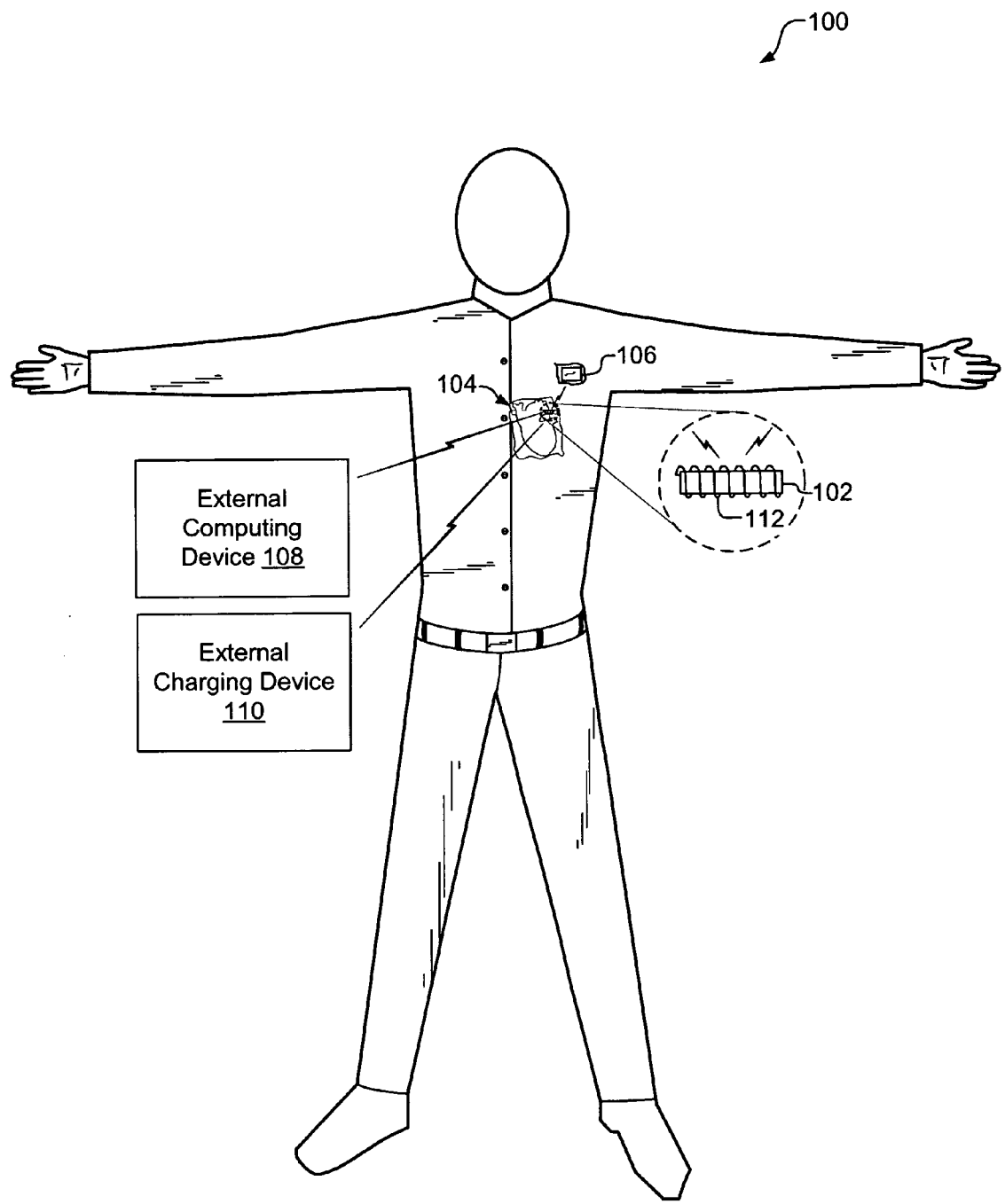
FIG. 1 illustrates a human patient with an implantable medical device (IMD) coupled to an inductive coil that is operable to provide communications to/from and/or to provide energy to the IMD.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

An implantable medical device (IMD) generally refers to any medical device that can be implanted in a human body to perform one or more of a sensing function or a therapeutic function. By way of example, but not limitation, an IMD may be operable to sense a physiologic parameter, such as blood pressure, temperature, posture, blood sugar level, or others. An IMD may be operable to provide therapy, such as pulses, or shocks to provide for rhythm management in a patient's heart. In addition to sensing and therapy, an IMD may provide other functions, such as communications functions.

FIG. 1 illustrates a human body 100 with an IMD, such as a physiologic sensor device 102, implanted in a peripheral vessel of the circulatory system of the body 100. In this embodiment, the physiologic sensor device 102 is operable to sense blood pressure at a location in the vessel. The sensor device 102 may store physiologic data (e.g., blood pressure measurements) and/or communicate the physiologic data or other data to other devices. For example, the sensor device 102 may be in communication with a manager device, which may be embodied in an implanted device or an external computing device 108.

In one embodiment, the manager device is a pulse generator (PG) 106 implanted in the human body 100. In this embodiment, the manager device provides therapy. For example, the pulse generator 106 generates pulses to provide therapy to the heart 104. By way of example, but not limitation, the pulse generator 106 may be a defibrillator or a pacemaker. The pulse generator 106 may also control or manage the physiologic sensor device 102 via communications to the sensor device 102.

Although the illustrated embodiment depicts a pulse generator 106 as an embodiment of an implanted manager device, it is to be understood that an implanted manager device does not need to be operable to provide therapy. Thus, in some embodiments, an implanted manager device only includes communication functionality to communicate with the sensor device 102. In some embodiments, the implanted manager device includes communication functionality to communicate with both the sensor device 102 and the external computing device 108.

Similarly, in the illustrated embodiment, the external computing device 108 includes communication functionality to communicate with the sensor device 102 and/or the PG 106. For example, the external computing device 108 can send commands or data to the sensor device 102, such as a command for the sensor device 102 to communicate sensor data, such as status or physiologic data.

The computing device 108 may be portable or stationary. By way of example, but not limitation, external computing device 108 may be a device worn on, or carried by, the human body 100. Alternatively, the external computing device 108 may be a general-purpose or special-purpose computer. Thus, examples of external computing devices are desktop computers, laptop computers, personal digital assistants (PDAs), cell phones, watches, or a computing device attached to a strap worn around the chest of the body 100. As is discussed further below, computing device 108 and PG 106 typically communicate wirelessly with the sensor 102.

An external charging device 110 may also emit a signal to the sensor device 102 that can be used to charge a battery in the sensor device 102. The external charging device 110 may include an inductive coil through which oscillating current can be generated, thereby creating an oscillating electromagnetic field in and around the charging device 110. As is discussed in further detail below, the electromagnetic field generated by the external charging device 110 can be detected by the sensor device 102 and used to charge a battery in the sensor device 102.

The external charging device 110 may be embodied in a handheld wand or probe, which a doctor, nurse, or other qualified person can position external to the body 100, but near the sensor device 102. As an alternative, the external charging device 110 may be woven into or carried in clothing worn on the body 100. As yet another alternative, the external charging device 110 may be a device positioned near or incorporated into the patient's bed, so that while the patient sleeps, the charging device 110 charges the battery of the sensor device 102.

As is also discussed in further detail below, the external charging device 110 can receive feedback signals from the sensor device 102, which indicate the status of recharging the battery in the sensor device 102. In this regard, the external charging device 110 may include a user interface whereby the user can determine status of recharging and move the charging device 110 to result in better charging, if necessary.

The sensor device 102 is coupled to a coil 112 that is used for communications and battery recharging. When oscillating current is generated in inductive coil 112, an oscillating electromagnetic field is generated in the vicinity of the inductive coil 112. For example, the electromagnetic field may arise through the aperture formed by the coil 112, and around loops of the coil 112. The electromagnetic energy can be used for wireless communications with the PG 106, the external computing device 108, and/or the external charging device 110.

Similarly, when electromagnetic energy is generated in or around the aperture of the inductive coil 112, electromotive force (EMF) is generated in the wire of the inductive coil 112. The EMF generated in the inductive coil 112 can be used for communication with the sensor device 102 and/or can result in current for recharging the battery in the sensor device 102. Thus, for example, an electromagnetic field generated by the external computing device 108 or the recharging device 110 can include field lines that cross loops of the inductive coil 112 to generate EMF in the wire of the inductive coil 112.

In some embodiments, the inductive coil 112 can be used to anchor the sensor 102 in position in the bodily vessel. As discussed further herein, the inductive coil 112 is made of a flexible, current-conducting, bio-compatible material, such as titanium, and the material may be coated with an outer layer of insulative material. In these embodiments, the coil 112 provides an expansive force against walls of the vessel to frictionally anchor or fix the coil 112, and the sensor 102 in position.

Figure 2:
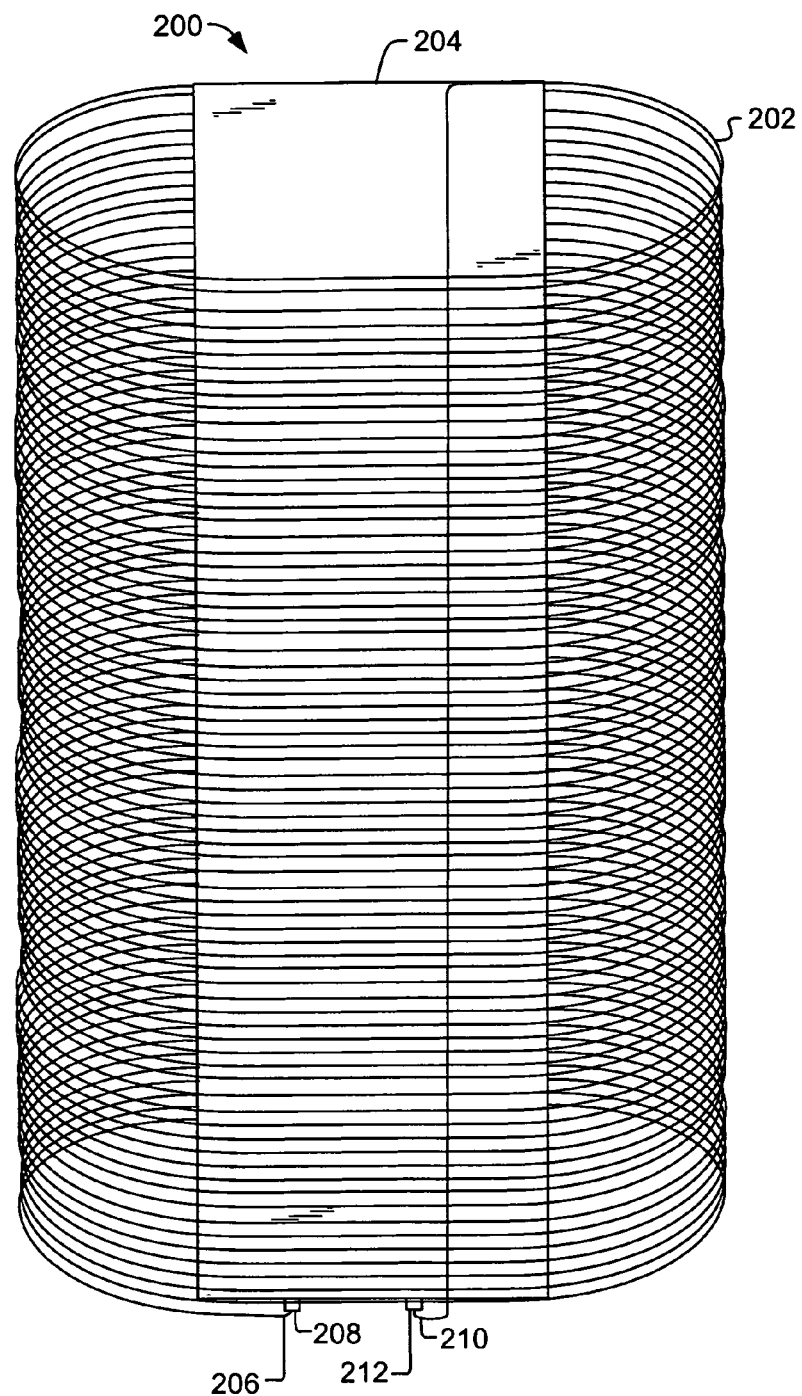
FIG. 2 illustrates an inductive coil disposed around and electrically coupled to an IMD.

FIG. 2 is an elevation view of an inductive coil 202 disposed around, and electrically coupled to, an implantable sensor device 200. In this embodiment, the sensor device 200 is positioned along a longitudinal axis and within an aperture formed by the coil 202. Opposite ends 206 and 210 of the inductive coil 202 are coupled to the sensor device 200. Electrode ends 206 and 210 extend through the sensor casing 204 via associated feedthroughs 208 and 212.

In accordance with various embodiments, feedthrough 208 and feedthrough 212 are electrically and fluidically insulative and may protrude through inner and outer sides of the casing 204. Feedthroughs 208 and 212 each have a narrow channel through which inductive coil ends 206 and 210 can extend. The inductive coil 202, casing 204, and feedthroughs 208 and 212 are typically composed of a biocompatible material.

Figure 3:
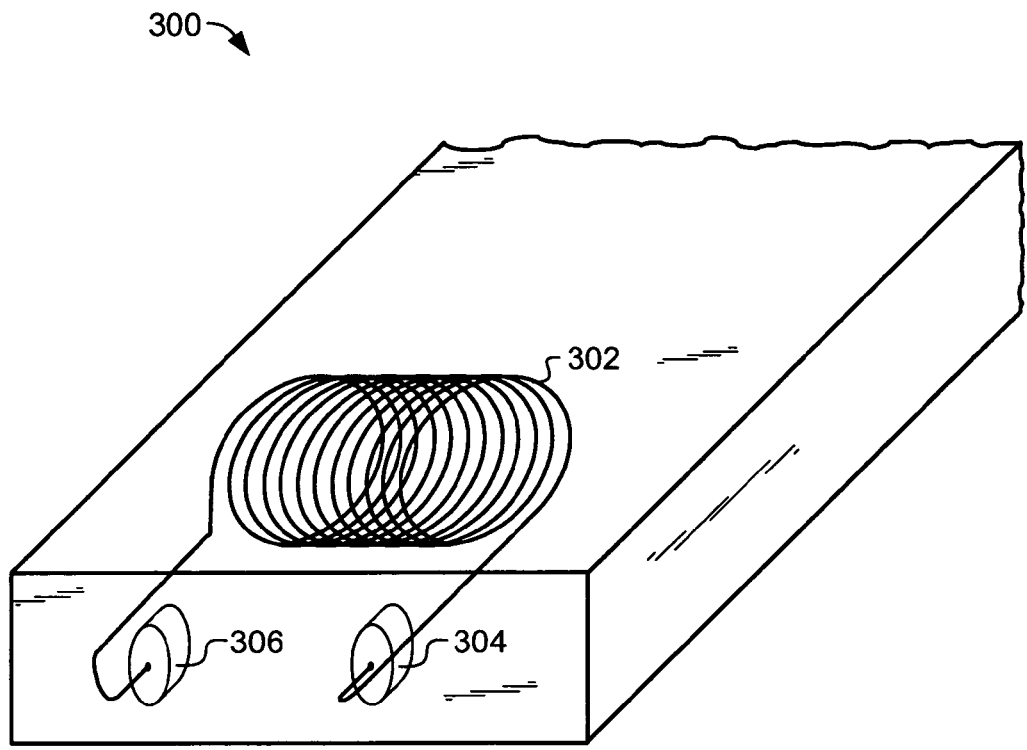
FIG. 3 illustrates a portion of an IMD with an inductive coil positioned adjacent thereto.

FIG. 3 illustrates a perspective view of a portion of an implantable sensor device 300 adjacent to an inductive coil 302, in accordance with another embodiment. In FIG. 3, the axis of the inductive coil 302 is transverse to the sensor device 300. Insulative feedthroughs 304 and 306 include corresponding passages through which opposite ends of the inductive coil 302 extend. Feedthroughs can be made of various types of biocompatible materials, such as, but not limited to, alumina, thermoplastic polyurethane (e.g., polyether based polyurethane, Tecothane®).

In the embodiment shown in FIG. 3, the inductive coil 302 does not provide an anchoring function, but provides for communication to/from and battery charging in the sensor device 300. FIGS. 2-3 are illustrative of only two possible shapes and orientations of inductive coils with respect to implantable medical devices. Numerous variations may be made, as may be known to those skilled in the art. For example, the feedthroughs may be located on different sides of the sensor casing, rather than the same wall as shown in FIGS. 2-3.

Figure 4:
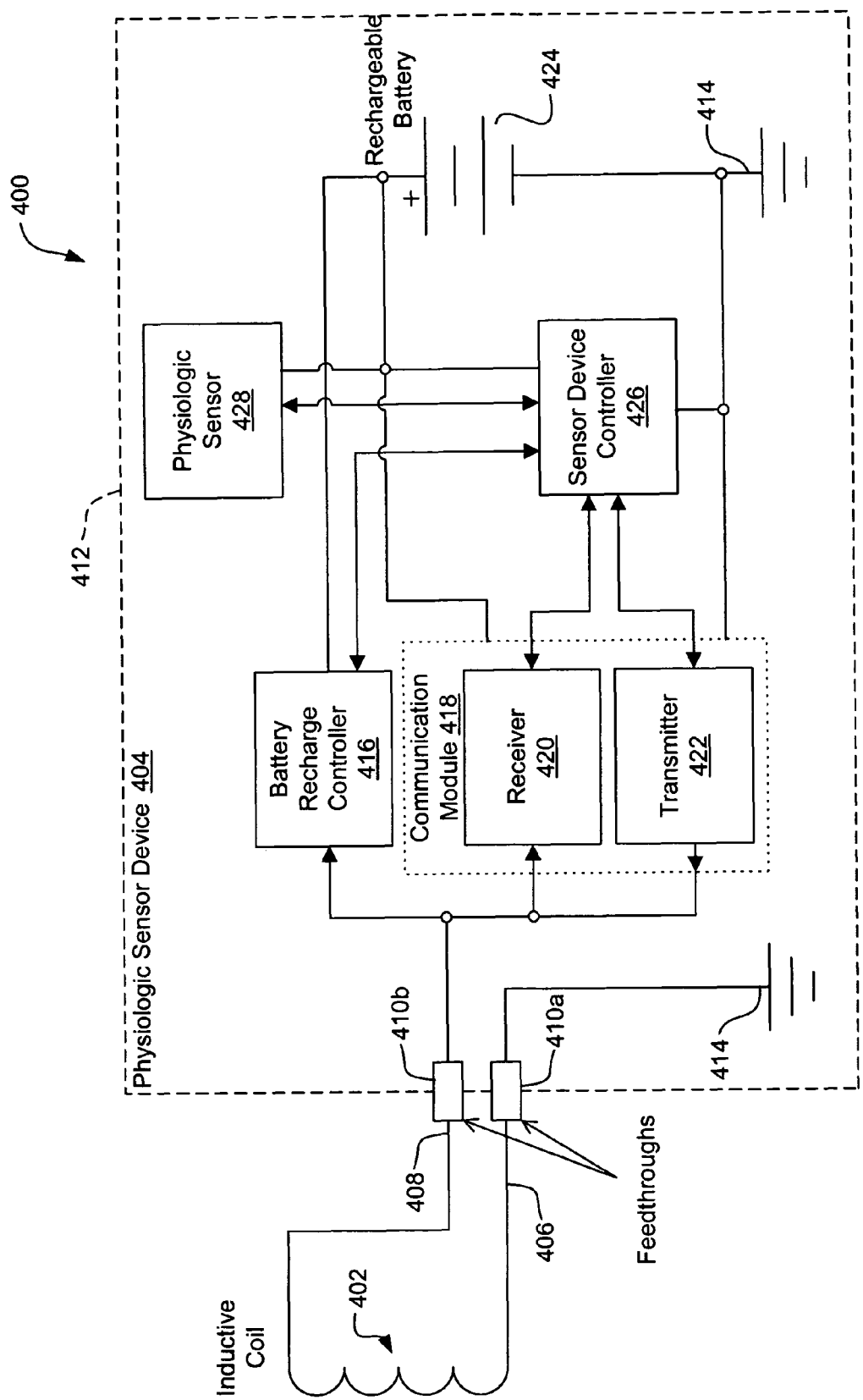
FIG. 4 is a schematic diagram illustrating an inductive coil coupled to an IMD in a single ended drive configuration.

FIG. 4 is a schematic diagram illustrating an inductive coil 402 coupled to an implantable sensor device 404 in a single ended drive configuration 400. The inductive coil 402 is made of biocompatible wire wound in a substantially cylindrical shape to enable an oscillating electromagnetic field to be generated within the aperture of, and/or around loops of, the coil 402. When an oscillating electromagnetic field is generated in and around the coil 402, EMF is generated in the wire of the coil 402. When oscillating current is generated in the coil 402, an oscillating electromagnetic field can be generated in and around the coil 402.

The inductive coil 402 has two electrodes at opposite ends of the coil 402: a first electrode 406 and a second electrode 408. The first electrode 406 and the second electrode 408 extend through associated feedthroughs 410a and 410b, respectively, and into the housing 412 of the implantable sensor device 404.

Within the housing 412, the first electrode 406 is coupled to a relative low voltage 414, referred to here as ground. The second electrode 408 is coupled to ports of a battery recharge controller 416 and a communication module 418. The implantable sensor device 404 can operate in at least two modes, including, but not limited to, a battery recharge mode and a communication mode. Depending on the mode, the coil 402 may be used for communication or for providing energy for battery recharging. In some cases, such as trickle charging, recharging and communication can occur simultaneously.

The communication module 418 includes a receiver 420 and a transmitter 422. Receiver 420 is operable to receive signals propagating through the second electrode 408. Transmitter 422 is operable to generate current through the coil 402 via the second electrode 408. Current transmitted onto the coil 402 causes electromagnetic energy to arise in and around the coil 402. The electromagnetic energy can be generated in such a way to form a wireless signal that can be detected and received by other devices. Signals transmitted by transmitter 422 may or may not be in a predefined format and follow a specified protocol. Signal format and protocol, if any, may be of an industry standard or a proprietary format and protocol.

Battery recharge controller 416 controls recharging of a battery 424. The battery 424 has an associated chemistry. In one embodiment, the battery 424 has a Lithium Manganese Dioxide ($Li/MnO_2$) chemistry. In other embodiments, other chemistries may be used, such as, but not limited to, $Li/Ag_x$-$V_yO_z$ or $Li/CF_x$, or $Li/SOCl_2$ or other non-lithium battery chemistries. Battery 424 is coupled to components in the implantable sensor device 404 to provide power to the components. For example, battery 424 is coupled to communication module 418, a sensor device controller 426, and a physiologic sensor 428. Typically, the battery 424 is not directly connected to other components, but rather indirectly connected.

The sensor device controller 426 controls the battery recharge controller 416, the communication module 418, and the physiologic sensor 428. As discussed above, the implantable sensor device 404 can operate in different modes. The sensor device controller 426 selects the mode of operation. In this regard, the sensor device controller 426 can command or otherwise cause the battery recharge controller 416 to recharge the battery 424 and can command or otherwise cause the communication module 418 to transmivreceive data. The sensor device controller 426 can also command or otherwise cause the physiologic sensor 428 to gather data and/or communicate data related to a physiologic parameter, such as blood pressure.

In some embodiments, commands and/or data can be sent to the implantable sensor device 404 from another device, such as an implanted communication device (e.g., therapeutic or nontherapeutic device) or an external computing device. In these embodiments, commands and/or data can be embodied in signals that are generated in the inductive coil 402 and received by receiver 420. Examples of commands are 'upload physiologic data', 'upload sensor device status data', or 'enter battery recharge mode'. When a command to upload data is received, the sensor control module 426 causes the requested data (e.g., physiologic or status) to be transmitted via transmitter 422. Current generated in the coil 402 oscillates to thereby cause an oscillating electromagnetic field to be generated that can be detected by a receiver of another implanted device or an external device, thereby enabling wireless communication of sensor device data.

When a command is received to enter battery recharge mode, the sensor device controller 426 can respond in a predetermined manner. In one embodiment, the sensor device controller 426 signals the battery recharge controller 416 to begin charging the battery 428 with energy arising in the inductive coil 402. The sensor device controller 426 may also command portions of the communication module 428 to deactivate during the battery recharging process. For example, the sensor device controller 426 may command the transmitter 422 to deactivate.

In some embodiments, the battery recharge controller 416 trickle charges the battery 428 using energy inherent in signals communicated via the inductive coil 402. For example, commands or data transmitted to the implantable sensor device 404 via the inductive coil 402 from an external computing device or an implanted pulse generator, or other implanted communication device, can be used to charge the battery 428, in addition to their primary function of communicating with the implantable sensor device 404. Thus, the implantable sensor device 404 can efficiently recharge the battery 428 using any energy that arises in the coil 402. As such, trickle charging is typically controlled by the sensor device controller 426.

The components of the implantable sensor device 404 may be implemented with hardware, software, firmware, or any combination of hardware, software, or firmware. For example, the sensor device controller 424 can include a microprocessor or microcontroller coupled to a memory that includes executable instructions readable by the microprocessor or microcontroller. As another example, communication module 418 may include circuitry having active and/or passive components typically used for receiving and transmitting data. As yet another example, the battery recharge controller 416 may include a rectifier to provide full wave or half wave rectification of the oscillating current. Components of the implantable sensor device 404 are typically selected based, at least in part, on the power requirements and the power rating of the battery 428.

Figure 5:
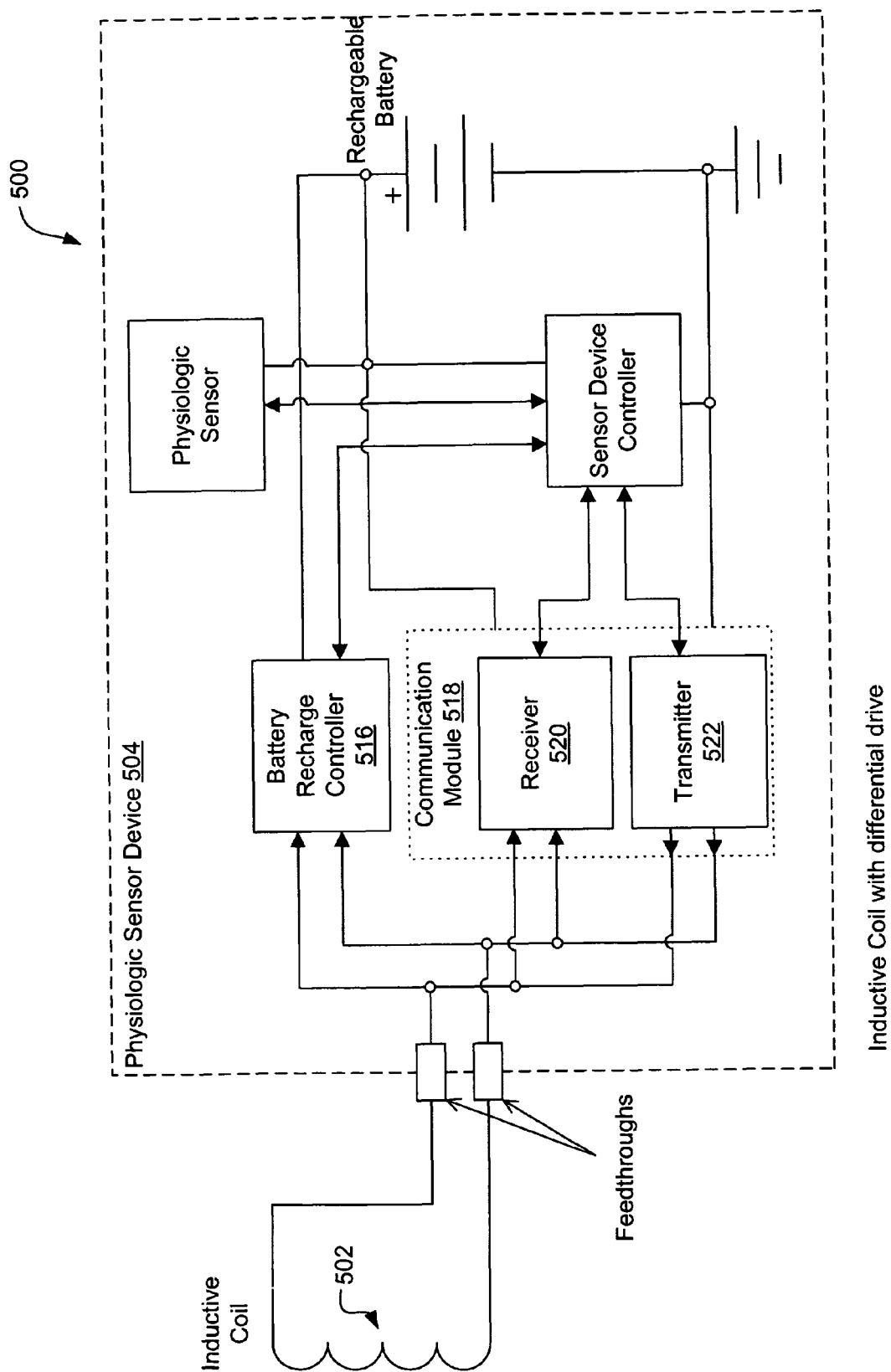
FIG. 5 is a schematic diagram illustrating an inductive coil differentially coupled to an IMD having exemplary components.

FIG. 5 is a schematic diagram illustrating an inductive coil 502 differentially coupled to an implantable sensor device 504 in a differential configuration 500. The sensor device 504 includes components similar to those shown and described above with respect to FIG. 4. One difference between the embodiment of FIG. 4 and the embodiment of FIG. 5 is with respect to the manner in which the inductive coil 502 is coupled to communication module 518 and battery recharge controller 516.

In the differential configuration 500 of FIG. 5, the first electrode 506 and the second electrode 508 of the inductive coil 502 are coupled to the battery recharge controller 516, the receiver 520, and the transmitter 522. In this fashion, the voltage across the components is the differential of the potential at opposite ends of the inductive coil 502.

Figure 6:
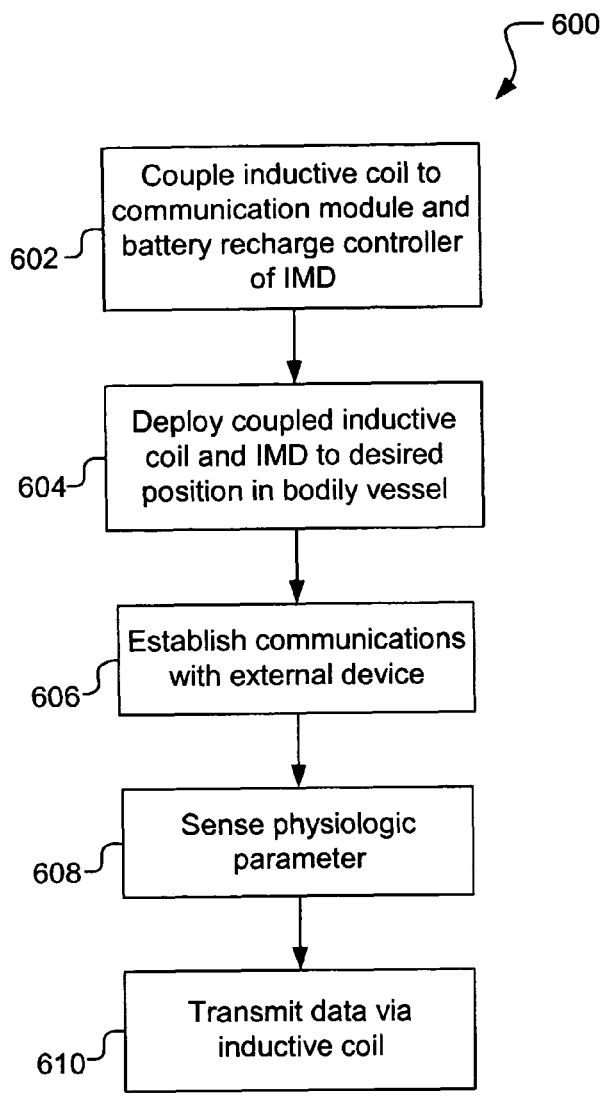
FIG. 6 is a flow chart illustrating an exemplary algorithm for using an inductive coil to mechanically anchor an IMD and to communicate with another IMD.

FIG. 6 is a flow chart illustrating an exemplary algorithm 600 for using an inductive coil to mechanically anchor an IMD, such as an implantable sensor device, in a bodily vessel and to communicate with the implantable sensor device. The algorithm 600 is not limited to the particular order of the operations shown in FIG. 6. In some cases, multiple operations can be combined into fewer operations. Some operations can be broken out into multiple operations.

Prior to deploying an implantable sensor device having an inductive coil for anchoring and communication, the inductive coil is coupled to the implantable sensor device in coupling operation 602. In one embodiment, coupling operation 602 involves indirectly coupling electrodes of the inductive coil to a battery recharge controller and communication module of the implantable sensor device. For example, the electrodes can be indirectly connected to the communication module with capacitors, or other passive components, in series, to provide any required signal conditioning.

The coupling operation 602 typically occurs during manufacture or assembly of the implantable sensor device, during which the two ends of the coil are fed through insulative feedthroughs in a wall of the implantable sensor device and connected to inputs/outputs of the implantable sensor device components. As discussed above, the inductive coil can be coupled in different ways, such as differentially coupled or coupled with single ended drive. The coupling operation 602 may also include stabilizing the coil on or around the implantable sensor device housing.

In a deploying operation 604, the inductive coil/sensor device assembly is deployed to a desired location in a bodily vessel. In one embodiment, the deploying operation 604 involves inserting the inductive coil/sensor device assembly into a catheter and catheterizing the patient. The catheter is guided to the desired location and the inductive coil/sensor device assembly is expelled from the end of the catheter.

When the inductive coil/sensor device is expelled from the catheter, in one embodiment, the coil self-expands within the vessel. When the coil expands, it presses against walls of the vessel to frictionally anchor the coil and the sensor device in the desired location. In another embodiment, balloon-deployment of the inductive coil/sensor device assembly can be used.

After the inductive coil/sensor device is deployed, an establishing operation 606 establishes communications with the sensor device. This may involve sending an initial signal to the sensor device from an external computing device or another communication module via the inductive coil and receiving a response from the sensor device, which is transmitted via the inductive coil. Signals can be sent to the sensor device by a communications module, which can create an electromagnetic field that crosses the inductive coil, thereby creating electromotive force (EMF) in the coil. The sensor device can generate a signal by generating oscillating current in the coil to create an electromagnetic field in and around the coil. After communications are established, a sensing operation 608 senses a physiologic parameter of interest. The sensing operation 608 may occur automatically at predetermined times, or in response to specified events or commands.

The sensor device transmits the data in a transmitting operation 610. Transmitting is performed by generating a signal through the inductive coil, which generates an electromagnetic field that can be detected wirelessly by a receiver of another device. The transmitting operation 610 can transmit physiologic data and/or other data, such as device status. In one embodiment, physiologic data is transmitted in real time, as the data is sensed in the sensing operation 608. During communication, the connections between the coil electrodes and the communication module may be periodically switched, depending on communication carrier frequency.

Figure 7:
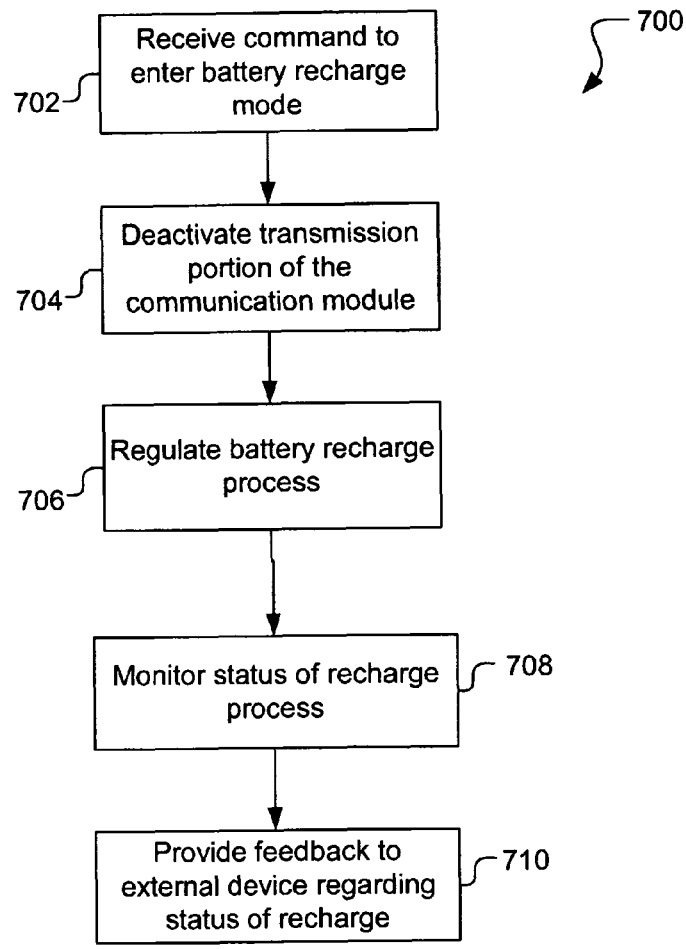
FIG. 7 is a flow chart illustrating an exemplary algorithm for using an inductive coil to charge a battery in an IMD.

FIG. 7 is a flow chart illustrating an exemplary algorithm 700 for using an inductive coil to charge a battery in an IMD. In one embodiment, the battery recharge algorithm 700 occurs after communication has been established between the IMD and another device. In a receiving operation 702, the sensor device receives a command to enter battery recharging mode. In response to receiving the battery recharge command, an optional deactivating operation 704 may deactivate a portion of the communication module, such as the transmitting portion.

During the battery recharging process, current is generated in the inductive coil. A regulating operation 706 regulates the process by managing power transmission to the battery in the sensor device. In addition, during or after the battery recharge process, a monitoring operation 708 monitors the status of the recharge. A providing operation 710 provides feedback regarding status of the battery recharge process. The providing operation 710 can transmit signals via the communication module to indicate whether the battery is successfully charging. The status could be received by an external recharging device and displayed on a user interface. Based on the displayed status, a user of the external recharging device can change the battery recharging process, for example by moving the recharging device, vary the power, and so on.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A system for communicating with a medical device implanted in a vessel of a human body, the system comprising:
    an implantable medical device (IMD);
    an inductive coil electrically coupled to the implantable medical device;
    the inductive coil configured to expand from a collapsed position, capable of delivery through the vessel, to an expanded position within the vessel, the inductive coil configured to frictionally engage a wall of the vessel and secure the implantable medical device within the vessel in the expanded position;
    the implantable medical device comprising a physiologic sensor device including a physiologic sensor, a casing having a number of feedthroughs electrically coupling the implantable medical device to the inductive coil, a rechargeable power source, a recharge controller configured for controlling recharging of the power source, communication circuitry operable to transmit and receive data via the inductive coil, and a sensor device controller configured for controlling data transmission and data reception by the communication circuitry;
    wherein electromotive force (EMF) is induced in the inductive coil when an oscillating electromagnetic field is created near the inductive coil; and
    wherein the sensor device controller is configured to detect a command from a manager device in communication with the IMD to enter a recharge mode of operation and to responsively deactivate at least data transmission by the communication circuitry via the inductive coil during the recharge mode of operation.

2. A system as recited in claim 1 wherein the rechargeable power source comprises a battery, and wherein the sensor device controller is further operable to monitor battery recharge status and cause the communication circuitry to transmit battery recharge status data via the inductive coil.

3. A system as recited in claim 1 wherein the battery recharge controller is differentially coupled to the inductive coil.

4. A system as recited in claim 1 wherein the inductive coil is self-expanding.

5. A system as recited in claim 1 wherein the inductive coil is balloon-deployable.

6. A system as recited in claim 1 wherein the IMD and the inductive coil are deployable through a catheter into the vessel.

7. A system as recited in claim 1 wherein the communication circuitry is operable to wirelessly transmit physiologic data to an implanted communication module via the inductive coil.

8. A system as recited in claim 7 wherein the communication circuitry transmits the physiologic data in response to a command from a pulse generator.

9. A system as recited in claim 1 wherein the EMF is generated by a second inductive coil outside the human body.

10. A system as recited in claim 9 wherein the second inductive coil is in a device carried by the human body.

11. A system as recited in claim 1 wherein the IMD comprises communication circuitry operable to transmit data via the inductive coil by generating electric current in the inductive coil.

12. A system as recited in claim 11 wherein the IMD further comprises a rechargeable battery, a physiologic sensor device, and a sensor device controller, and wherein the sensor device controller is operable to deactivate at least a portion of the communication circuitry while the battery is being recharged.

13. A system as recited in claim 12 wherein the sensor device controller is operable to receive a recharge command from an external device commanding the IMD to enter a battery recharge mode.

14. A system as recited in claim 1 wherein the recharge controller is operable to trickle charge the rechargeable power source using energy from communications received via the inductive coil.

15. A method for gathering physiologic data related to a physiologic parameter in a human body, the method comprising:
    communicably coupling an inductive coil to communication circuitry of an implantable medical device (IMD);
    deploying the inductive coil and the IMD into a vessel of the human body, the inductive coil configured to expand from a collapsed position, capable of delivery through the vessel, to an expanded position within the vessel, the inductive coil configured to frictionally engage a wall of the vessel and secure the IMD within the vessel;
    sensing physiologic data within the body via a physiologic sensor of the IMD;
    inducing current in the inductive coil via the communication circuitry, the current generating an electromagnetic field comprising a signal representative of the sensed physiologic data;
    detecting a command from a manager device in communication with the IMD to enter a recharge mode of operation and recharging a rechargeable power source of the IMD using energy from the inductive coil; and
    monitoring a recharge status of the power source and transmitting recharge status data via the communication circuitry to the manager device.

16. A method as recited in claim 15 wherein recharging the power source and inducing current via the communication circuitry are simultaneous.

17. A system for gathering physiologic data related to a human body, the system comprising:
    a sensor device implanted in the human body, the sensor device including a rechargeable power source and communication circuitry operable to transmit and receive data;
    an expandable inductive coil disposed at least in part around and communicably coupled to the implanted sensor device, the inductive coil configured to frictionally secure the sensor device within the human body;
    a manager device in communication with the implanted sensor device via the inductive coil; and
    wherein the sensor device is configured to detect a command from the manager device to enter a recharge mode and to responsively deactivate data transmission by the communication circuitry via the inductive coil.

18. A system as recited in claim 17 wherein electrodes of the inductive coil are disposed through insulative feedthroughs positioned in a wall of the implanted sensor device, the feedthroughs allowing the electrodes to be fed through the wall of the implanted sensor device.

19. A system as recited in claim 18 wherein the each feedthrough is composed of a bio-compatible insulator.

20. A system as recited in claim 17 wherein the inductive coil comprises a stent-like structure coiled around the implanted sensor device, wherein the stent-like structure expands against walls of a vessel in the human body to provide fixation within the vessel.

21. A system as recited in claim 17 wherein the inductive coil comprises an attachment to the implanted sensor device.

22. A system for implanting a sensor device in a human body, the system comprising:
  a sensor device including a casing that houses a communication module, a battery recharge module, a sensor operable to sense a physiologic parameter, and a rechargeable battery;
  an expandable inductive coil electrically coupled to the sensor device and configured to frictionally secure the sensor device at a location in the human body, wherein the inductive coil provides communication and energy delivery to the sensor device; and
  wherein the sensor device is configured to monitor battery recharge status and prompt the communication module to transmit battery recharge status data via the inductive coil.

* * * * *